United States Patent [19]

Bouck

[11] 4,366,700
[45] Jan. 4, 1983

[54] APPARATUS FOR MEASURING THE DIFFERENTIAL PRESSURE OF DISSOLVED GASES IN A FLUID MEDIUM

[76] Inventor: Gerald Bouck, 12609 NE - 5th St., Bellevue, Wash. 98005

[21] Appl. No.: 270,040

[22] Filed: Jun. 3, 1981

[51] Int. Cl.³ .................... G01N 7/00; B01D 13/00
[52] U.S. Cl. ........................................ 73/19; 55/158
[58] Field of Search ................... 73/19; 55/158, 270

[56] References Cited

U.S. PATENT DOCUMENTS

| | | | |
|---|---|---|---|
| 3,040,561 | 6/1962 | Wright | 73/19 |
| 3,060,726 | 10/1962 | Weber | 73/19 |
| 3,871,228 | 3/1975 | Weiss | 73/19 |
| 3,977,232 | 8/1976 | Hickam et al. | 73/19 |
| 4,129,029 | 12/1978 | Moll et al. | 73/19 |
| 4,150,560 | 4/1979 | Wieland | 73/19 |
| 4,179,918 | 12/1979 | Van Strien | 73/19 |
| 4,255,963 | 3/1981 | Down | 73/19 |

*Primary Examiner*—Edward R. Kazenske
*Assistant Examiner*—David V. Carlson

[57] ABSTRACT

The disclosed invention, a gasometer, measures the total dissolved gas pressure in a fluid in relation to the ambient atmospheric pressure, thus determining the relative saturation of dissolved gases in the liquid. In prior devices, bubbles have caused inaccurate readings, thus requiring that an operator be present during operation to manually clear bubbles. This gasometer is an improvement over previous devices in that it allows continuous and automatic monitoring of the dissolved gas pressures in the fluid by greatly reducing or eliminating the formation of bubbles in the apparatus. The formation of bubbles is prevented by selectively pressurizing the testing chamber using inlet and outlet valves at either end to selectively vary the pressure. The gasometer containing a pressurized chamber is inserted into the fluid transport system. Located in the interior of the chamber is semipermeable tubing which allows gas to pass through to its interior, but which excludes the fluid. The migrated gas inside the tubing comes to equilibrium with the dissolved gas in the fluid, at which time the relative pressure between the atmosphere outside the tubing and within the system is measured with a device such as a manometer or other pressure measuring device.

4 Claims, 6 Drawing Figures

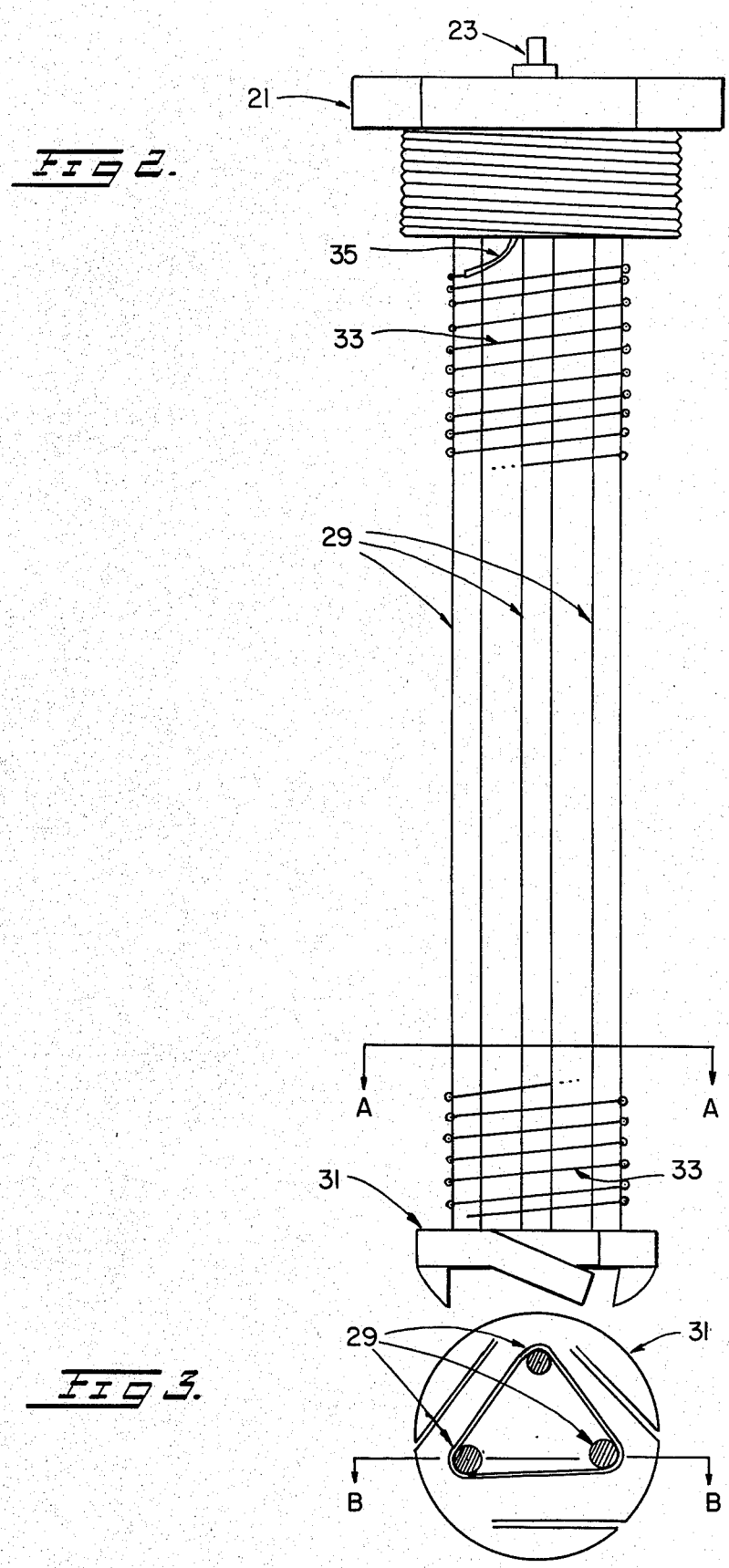

APPARATUS FOR MEASURING THE DIFFERENTIAL PRESSURE OF DISSOLVED GASES IN A FLUID MEDIUM

BACKGROUND OF THE INVENTION

1. Field of the Invention

This invention relates to the field of gas pressure measurement, and in particular the measurement of the differential pressure of dissolved gases in fluids.

2. Description of the Prior Art

Prior art have used a semipermeable membrane enclosure inserted in the fluid to allow the gas to migrate through the membrane and reach equilibrium with the pressure of the dissolved gases in the fluid. The pressure in the interior of membrane enclosure is then measured. One problem with a number of the previous devices has been inaccurate readings due to the formation of bubbles on the membrane when the fluid is supersaturated with dissolved gases. A second problem has been leaks developing within the system causing the devices to malfunction. A third problem has been that prior devices have required continuous monitoring by a technician to insure that the system functions properly and to dislodge accumulated bubbles. The disclosed invention solves these problems by pressurizing the chamber where the measurements are taken, thus inhibiting the formation of bubbles. The second problem is solved by having the fluid being measured separated from the pressure measuring means in a sealed chamber. In regard to the third problem, this disclosed invention is an improvement over the prior art in that since the subject invention is installed as a part of the fluid transport system, reduces the formation of bubbles, and operates continuously and automatically, no technician is required to be on constant standby during the operation of the invention.

BRIEF SUMMARY OF THE INVENTION

The disclosed invention, a gasometer, provides a device for continuously and automatically measuring the dissolved gas pressure in a fluid transport system. The gasometer has a pressurizable chamber which can be installed in a fluid transport system, such as in the piping in the system. Inside the chamber is a tubular-shaped semipermeable membrane which is in contact with the pressurized fluid. This membrane allows the passage of dissolved gases, but prohibits the passage of the fluid, to the interior of the tubing where equilibrium is attained between the gases in the fluid and in the tubing. The pressurizable chamber can be variable pressurized by inlet and outlet valves to prevent the formation of bubbles on the semipermeable membrane, thus making the results more accurate. The tubing is connected to the exterior of the chamber by an impermeable means where the pressure can be measured on a device such as a manometer, or recording pressure guage.

It is an object of this invention to provide an accurate means of determining the differential dissolved gas pressure of a gas in a fluid medium.

It is a further object of the invention to provide a means of continuous measurement of the differential dissolved gas pressure of a gas in a fluid medium.

It is yet a further object of this invention to provide an automatically operated means of measuring the differential dissolved gas pressure of a gas in a fluid medium.

It is yet a further object of this invention to provide a low maintenance apparatus for measuring the differential dissolved gas pressure of a gas in a fluid medium.

BRIEF DESCRIPTION OF THE DRAWINGS

FIG. 2 is a schematic front view of the internal components of the gasometer.

FIG. 3 is a cross section A—A view of FIG. 2 showing the base plate and the location of the three support members and a portion of the semipermeable tubing wrapped around the support members.

DETAILED DESCRIPTION OF THE PREFERRED EMBODIMENT

Figure 1:
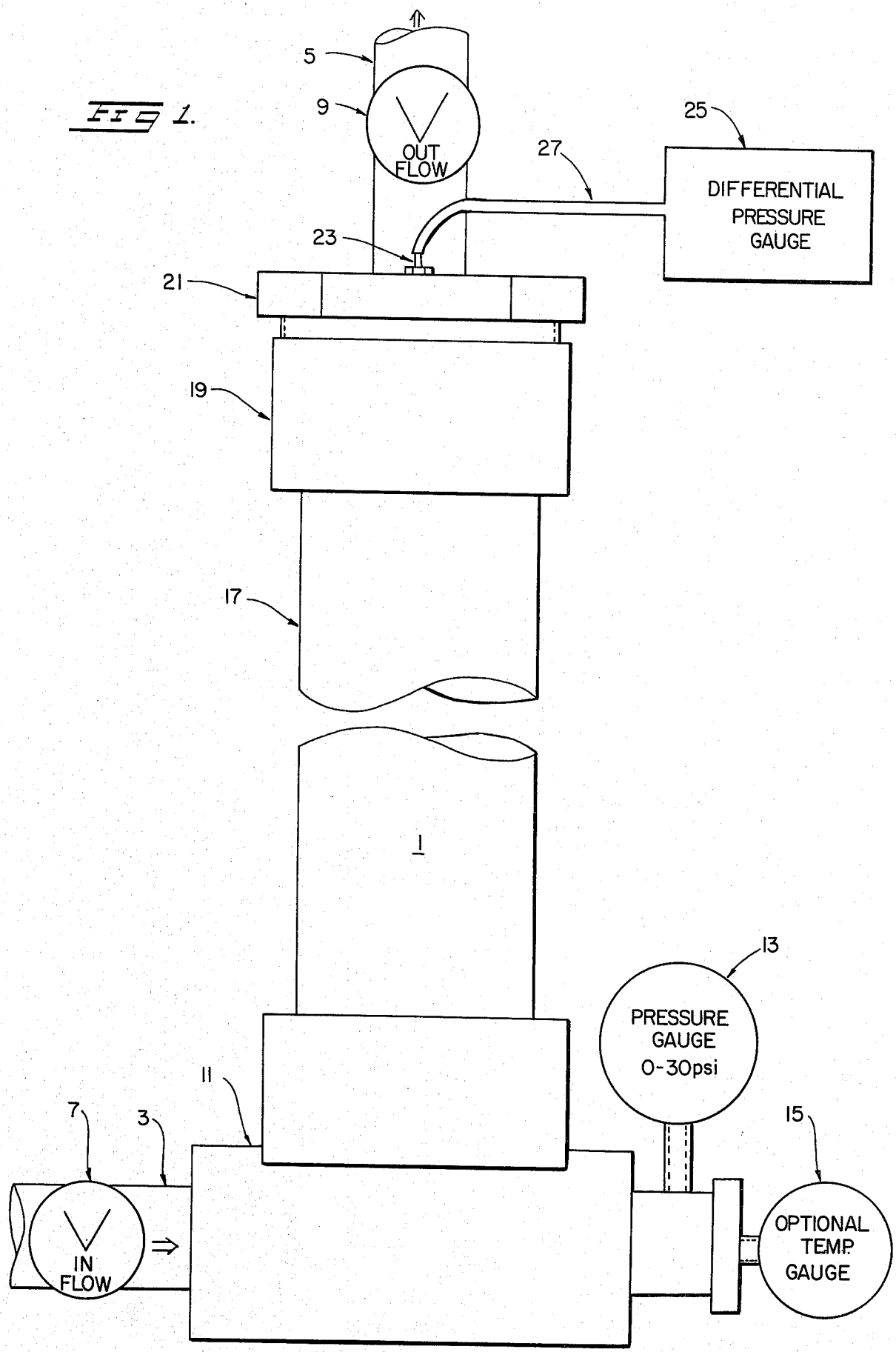
FIG. 1 is a schematic front view of the completely assembled and installed gasometer.
Figure 5:
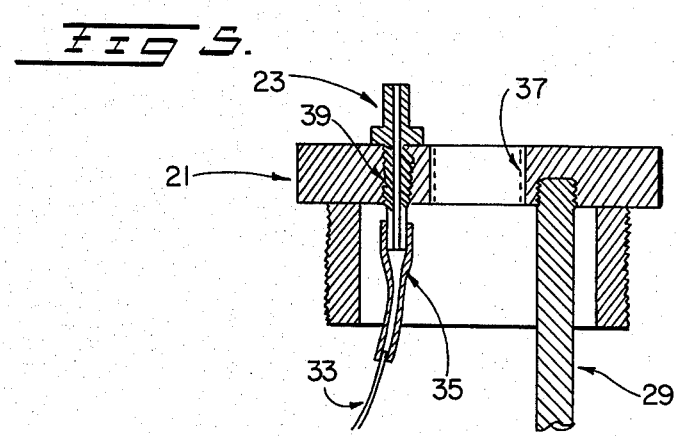
FIG. 5 is a fragmentary cross section C—C view of FIG. 4 showing the preferred embodiment of the cap with the support members and the passage detailed therein.

FIG. 1 shows the front view of the completely assembled and installed gasometer 1, installed between pipes 3 and 5 in a fluid transport system. Connected to inflow pipe 3 is an inflow valve 7, and to outflow pipe 5, an outflow valve 9, so that when said valves are operated in combination, the pressure inside the gasometer can be regulated. The selective pressurization of the gasometer by valves 7 and 9 prevents the formation of bubbles on semipermeable tubing 33. The bottom portion of the gasometer chamber consists of a Tee joint conduit connector 11. The first opening is connected to inflow pipe 3. The second opening is adopted for connection of a pressure gauge 13 and optional temperature gauge 15. The third opening communicates with the interior of the gasometer 1 and is attached, such as with a solvent weld, to a translucent tubular sleeve 17. This translucent tubular sleeve 17, which is of sufficient size and diameter to accept the interior assembly of the gasometer and forms the middle portion of the chamber, is clear so that direct observation can be made of the interior of the chamber to monitor the formation of bubbles. The upper portion of the gasometer chamber consists of a tubular adapter 19, the lower portion of which is connected to the translucent sleeve 17, such as with a second solvent weld, and the upper portion of which has internal threads to accept the cap 21. The cap 21 in turn has external threads and is secured into the adapter 19. As shown in FIG. 5, the cap 21 has a concentric threaded passage 37 to which the outlet pipe 5 is connected, and a second threaded passage 39 through which a threaded center bore coupling 23 is sealably inserted to provide communication between the interior and exterior of the chamber. As shown in FIG. 1, the exterior end of the coupling communicates with a differential pressure measuring means 25 such as a manometer or a recording pressure gauge by means of an impermeable flexible hose 27.

Figure 4:
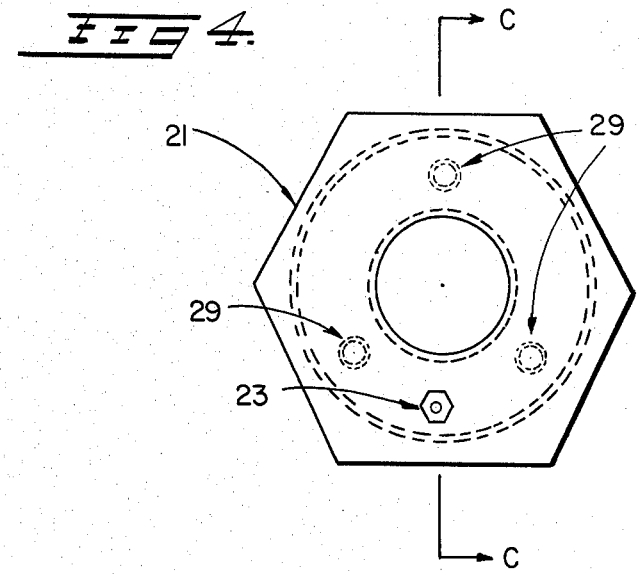
FIG. 4 is a top schematic view of FIG. 2 showing the internal components of the gasometer.
Figure 6:
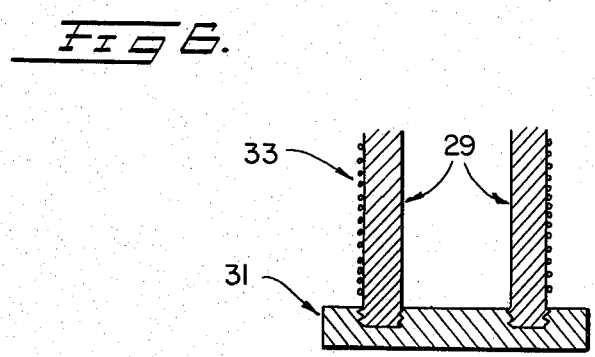
FIG. 6 is a fragmentary cross section B—B view of FIG. 3 showing the preferred method of attaching the support members to the base plate.

FIGS. 2–6 show the internal assembly of the gasometer. The internal assembly is mounted on the underside of the cap 21 and consists of a plurality of support members 29, base plate 31, semipermeable tubing 33, and impermeable tubing 35. As shown in FIG. 5, The upper ends support members 29 are threadably mounted in underside of the cap 21. As shown in FIGS. 3 and 4, the support members 29 are equidistantly spaced and project downward, parallel to each other, and as shown in FIG. 6, are threadably mounted to the base plate 31 which has openings adopted to allow passage and mixing of entering fluids. FIGS. 2 and 3 show the semipermeable tubing 33 spirally wrapped around the support members 29, with the bottom end of the tubing 33 sealed and attached to one of the support members 29 near the base plate 31. FIGS. 2 and 5 show the upper end of the semipermeable tubing 33 sealably attached to the impermeable tubing 35 such that their respective interior passages are in communication.

As shown in FIG. 5, the impermeable tubing 35 is sealably mounted onto the coupling 23 such that their interior passages are in communication, thus allowing the gases that migrate through to the interior of the semipermeable tubing 33 to ultimately be in communication with the differential pressure measuring means 25 located exterior to the chamber.

I claim:

1. An apparatus for measuring dissolved gas pressure in a fluid to determine the level of gas saturation of said fluid, comprising:
    a cylindrical container defining a testing chamber for enclosing a semipermeable tubing, said container connected into a fluid communication system;
    said semipermeable tubing being hollow for transmission of gases through to the interior of the tubing but prohibiting the passage of the fluid to the tubing interior, the bottom end of said tubing being closed and the top end fastened to a means for communicating the interior of the tubing with a differential pressure gauge outside of the container;
    a means for supporting the semipermeable tubing inside the testing chamber in a closely spaced spiral shape;
    said differential pressure gauge measuring the pressure difference between the interior of the first tube and the atmosphere;
    an inlet and outlet valve connected between each end of said container and the fluid communication system and
    said valves selectively pressurizing the testing chamber for inhibiting the formation of bubbles on the semi-permeable tubing inside the chamber.

2. The apparatus of claim 1 wherein the cylindrical container for enclosing a semipermeable tubing comprises:
    A cylindrical cap having a means on the bottom outer circumference for connection to a cylindrical sleeve, said cap having a first opening in the upper center portion of said cap for the passage of fluid and for attachment to a fluid outlet means for exit of fluid, and a passage for closely passing the means for communicating between the interior portion of the chamber and said differential pressure gauge for measuring the pressure difference;
    said cylindrical sleeve being of sufficient diameter and length to enclose the spiraled semipermeable tubing, the top portion connected to the cylindrical cap and the bottom portion having a means for attachment to a fluid inlet means for entrance of fluid;
    said inlet valve having one end connected to the bottom portion of said sleeve and the second end connected to the inflowing portion of a fluid transport assembly, and
    said outlet valve having one end connected to the cylindrical cap, the other end connected to the discharge portion of the fluid transport assembly, said inlet and outlet valve regulated to variably pressurize the container.

3. The apparatus of claim 2 wherein the means for supporting the semipermeable tubing comprises:
    a plurality of support members, the top ends of which are attached to the underside of the cap, the bottom ends of which are attached to a base plate, the support members mounted so that each is parallel to the other;
    said base plate having the support members attached thereto, having an opening therein for passage and mixing of fluid, the bottom closed end of the tubing mounted near the base plate with the tubing closely wrapped in an upward spiral around the plurality of support members, said spiral ending near the cap, with the top end of the tubing connected to the means for communicating between the interior and the differential pressure gauge.

4. The apparatus of claim 2 wherein the means for communicating between the interior and said differential pressure gauge comprises:
    a flexible impermeable tube, one end of which is connected to the semipermeable tubing such that the interior portions of each are in communication, and the other end of which is connected to a coupling with a center bore, said coupling mounted in a passage in the cap;
    said coupling having a center bore sealably mounted in the passage in the cap, the portion of said coupling on the interior communicating with the impermeable tubing, and the portion on the outside the chamber communicating with the differential pressure gauge.

* * * * *

UNITED STATES PATENT AND TRADEMARK OFFICE
CERTIFICATE OF CORRECTION

PATENT NO. : 4,366,700

DATED : January 4, 1983

INVENTOR(S) : Gerald Bouck

It is certified that error appears in the above-identified patent and that said Letters Patent is hereby corrected as shown below:

On The Title Page Insert:

-- [73] Assignee: The United States of America as represented by the Secretary of the Interior --.

Signed and Sealed this

Second Day of August 1983

[SEAL]

Attest:

GERALD J. MOSSINGHOFF

Attesting Officer

Commissioner of Patents and Trademarks